(12) United States Patent
Davankov et al.

(10) Patent No.: US 6,527,735 B1
(45) Date of Patent: Mar. 4, 2003

(54) METHOD OF PERITONEAL DIALYSIS

(75) Inventors: Vadim Davankov, Moscow (RU); James Brady, Riverdale, NY (US); Nathan Levin, New York, NY (US)

(73) Assignee: RenalTech International LLC, New York, NY (US)

( * ) Notice: Subject to any disclaimer, the term of this patent is extended or adjusted under 35 U.S.C. 154(b) by 0 days.

(21) Appl. No.: 09/560,312

(22) Filed: Apr. 27, 2000

(51) Int. Cl.⁷ .................................................. B01J 20/26
(52) U.S. Cl. ......................................... 604/29; 604/6.09
(58) Field of Search ........................... 604/29, 5.04, 6.09

(56) References Cited

U.S. PATENT DOCUMENTS

| | | | | |
|---|---|---|---|---|
| 3,825,493 A | * | 7/1974 | Brown et al. .................. 604/29 |
| 4,183,811 A | * | 1/1980 | Walch et al. ................. 210/646 |
| 4,276,175 A | * | 6/1981 | Bower ......................... 210/636 |
| 4,303,068 A | * | 12/1981 | Zelman .......................... 604/5 |
| 4,312,757 A | * | 1/1982 | Brumfield .................... 210/646 |
| 4,765,907 A | * | 8/1988 | Scott ........................... 210/648 |
| 4,775,482 A | * | 10/1988 | Thurman ..................... 210/668 |
| 4,861,485 A | * | 8/1989 | Fecondini .................... 210/641 |
| 5,079,274 A | * | 1/1992 | Schneider et al. ........... 521/146 |
| 5,545,131 A | * | 8/1996 | Davankov ....................... 604/5 |
| 5,773,384 A | * | 6/1998 | Davankov et al. ........... 502/402 |
| 5,944,684 A | * | 8/1999 | Roberts et al. ................. 604/5 |
| 5,980,481 A | * | 11/1999 | Gorsuch ....................... 604/28 |
| 6,114,466 A | * | 9/2000 | Davankov et al. ......... 525/332.2 |
| 6,136,424 A | * | 10/2000 | Davankov et al. ........ 428/305.5 |
| 6,254,567 B1 | * | 7/2001 | Treu et al. .................... 604/29 |

* cited by examiner

*Primary Examiner*—John Fox
(74) *Attorney, Agent, or Firm*—I. Zborovsky

(57) ABSTRACT

A method of peritoneal dialysis includes introducing a dialysis solution into a peritoneal cavity; allowing the dialysis solution to dwell in the peritoneal cavity for a period of time to provide diffusion through an inner lining of an abdominal cavity with exchange of components between a microcirculation of a peritoneum and a dialysis fluid; withdrawing the dialysis solution from the peritoneal cavity with toxins; passing the dialysis solution with toxins through an absorbent polymeric material which has a size, shape, and structure selected so as to remove the toxins in a molecular range of 300–30,000 Dalton from the spent dialysis solution; and returning the thusly purified peritoneal dialysis solution to the patient.

4 Claims, 1 Drawing Sheet

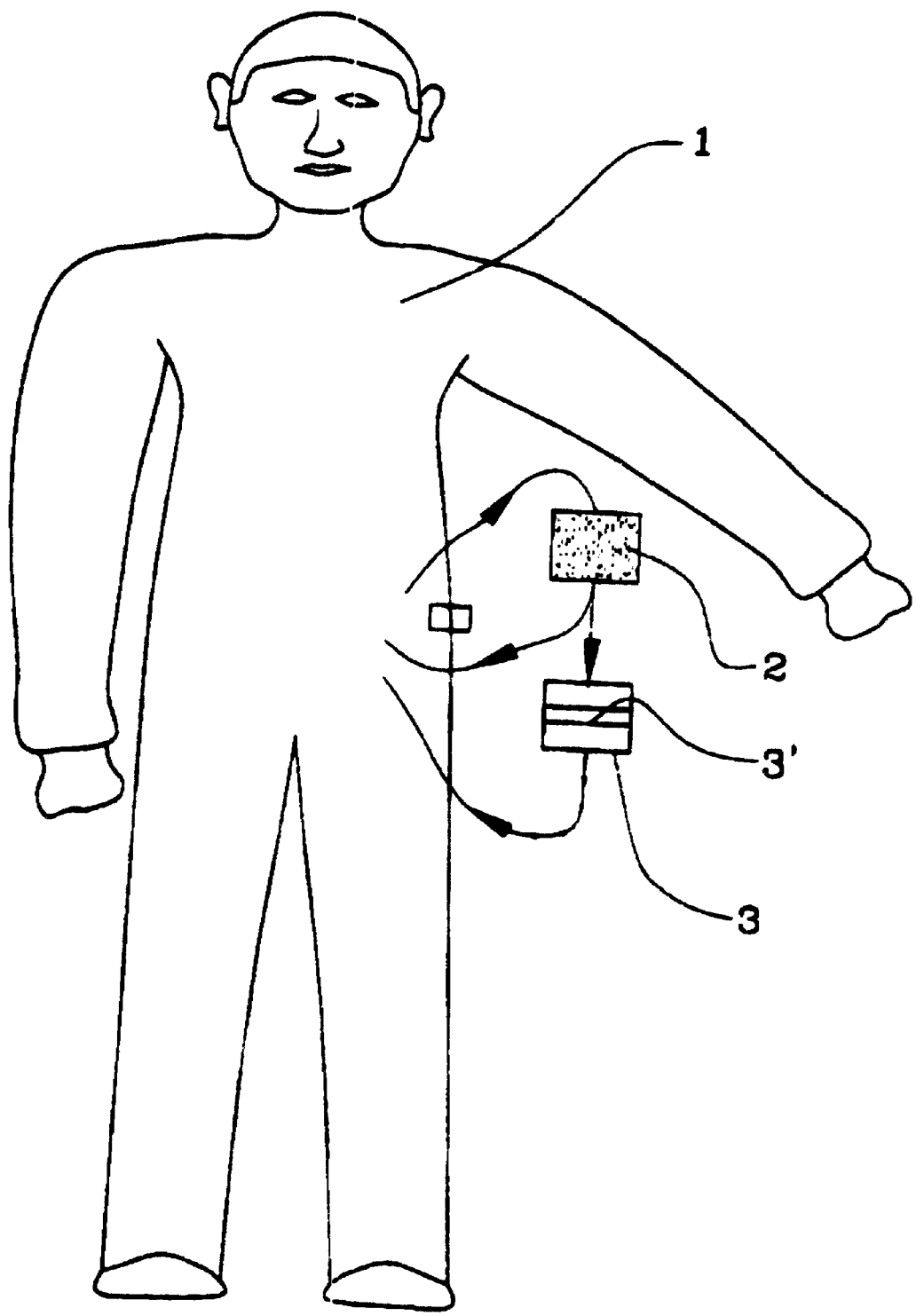

METHOD OF PERITONEAL DIALYSIS

BACKGROUND OF THE INVENTION

The present invention relates to methods of peritoneal dialysis.

It is well known that all physiological liquids, e.g., blood and peritoneal fluid, accumulate and transport various toxins. These toxins are gradually processed by the liver and kidney. However, these organs are directly exposed to the action of toxins and their function may become impaired. It is therefore necessary to remove the toxins from the physiological liquids by treating them, e.g., in a special extracorporeal circuit. In the case of kidney and liver failure, it is especially important to provide efficient removal of toxic metabolic products.

A plurality of methods have been invented and have been utilized for removing toxins from blood or blood plasma. One of the most efficient such methods is dialysis. Dialysis, however is generally restricted to removing small toxic molecules, whereas so-called middle molecular weight toxins are eliminated inefficiently, even with more modern high-flux dialysis membranes.

It has been also proposed to remove toxins, both of small and larger size, with peritoneal solutions. A special solution, called peritoneal dialysate, is introduced into the peritoneal cavity through a permanent indwelling catheter placed in the abdominal wall. Dialysate in the amount of 2–3 liters fills the peritoneal cavity and dwells there for a period of time. During this period, intensive diffusion through the inner lining of the abdominal cavity (the peritoneal membrane) takes place under an osmotic pressure differential, so that components, including toxic ones, are exchanged between the microcirculation of the peritoneum and the dialysate fluid. Excess water, too, is removed from the body, when hyperosmotic dextrose (glucose) concentration in the dialysate solution is applied to effect the desired liquid transfer through the peritoneal membrane. Dialysate is drained from the peritoneal cavity thus removing excess water and dissolved toxic compounds.

Most peritoneal dialysis (PD) is performed as Continuous Ambulatory Peritoneal Dialysis (CAPD) where 3–4 exchanges of approximately 2 liters of fluid per exchange are preferred during the day and at night, with the dwell time of dialysate amounting up to 4–6 hours, and one 8-hour exchange overnight. It is also possible to use an automated fluid delivery system that performs the entire procedure automatically, as in Continuous Cyclic Peritoneal Dialysis (CCPD).

Water used to make the dialysate is ultrapure and is typically produced through reverse osmosis. The typical composition of dialysate is as follows:

Glucose (g/dL)
1.5–2.5
Sodium (mEq/L)
118–132
Potassium (mEq/L)
0
Calcium (mEq/L)
3.5
Magnesium (mEq/L)
1
Lactate (mEq/L)

After a single PD session is over, the spent fluid is discarded. With approximately 45,000 patients using PD every day in U.S. alone, the amount of PD fluid is significant. Another significant problem from an environment concern is the plastic containers that hold the fluid. Millions of these containers are discarded each year. Because of these problems, regeneration of the dialysate fluid and its reuse by reinfusing to the same patient is highly desirable. A feasible way would be to subject the dialysate fluid to purification, which removes, through a semi permeable membrane, excess water and small toxic molecules. This technique however, would have the same limitations that hemodialysis has, namely, that clearance of middle-size molecules, including several toxic proteins, through the membrane is slow and incomplete. Reusing the peritoneal dialysis fluid would thus result in the large toxic molecules to build up in the organism, which is characteristic of kidney failure patients on a permanent hemodialysis treatment.

SUMMARY OF THE INVENTION

Accordingly, it is an object of the present invention to provide a new method of peritoneal dialysis which is a further improvement of the existing methods.

In keeping with these objectives and with others which will become apparent hereinafter, one feature of the present invention resides, briefly stated, in a method of peritoneal dialysis which includes introducing dialysis solution into a peritoneal cavity; allowing the solution to dwell in the peritoneal cavity for a period of time to provide diffusion through an inner lining of an abdominal cavity with exchange of components between a microcirculation of a peritoneum and a dialysis fluid; withdrawing the dialysate from the peritoneal cavity, passing the spent dialysate with toxins through a material which has the size, shape, and structure selected so as to remove the toxins in a molecular range of 300–30,000 Dalton from the spent dialysis fluid; and returning the thusly purified peritoneal dialysis solution to the patient.

When the method is performed in accordance with the present invention, the reuse of the dialysis solution provides a significant economy of the peritoneal fluid. Discarding of the bags which accommodate the solution is drastically reduced.

Another advantage of reuse of the dialysate liquid is that, besides the toxic components that need to be removed, the liquid also contains large molecular weight proteins, first of all, albumin, that have been gradually released into the dialysate liquid through the peritoneal membrane during the dwelling period. These essential components of physiological liquids of the organism get los when the dialysate liquid is discarded, and the organism has to compensate for the loss by an intensified protein synthesis. If only small and middle size toxic species could be removed from the used dialysate, but not the albumin-type higher essential proteins, the reuse of the thus purified liquid would significantly reduce further migration and loss of these proteins with the dialysate liquid, due to a diminished concentration gradient between the dialysis liquid and the body tissue with respect to the above essential high molecular weight proteins.

In accordance with another feature of the present invention, the method further includes additionally passing the spent dialysis fluid with toxins along a dialysis membrane for removing excess water and small toxic molecules, before returning the spent and purified dialysate fluid to the patient.

In accordance with another feature of present invention, said passing includes passing the dialysis fluid through the material which is a porous hydrophobic polymer with an enhanced proportion of pores in a diameter range between 1 and 10 nm.

In accordance with a further feature of present invention, the porous hydrophobic polymer is a copolymer of a crosslinked divinyl compound selected from the group consisting of divinylbenzene and diisopropenylbenzene and a monovinyl compound selected from the group consisting of styrene, ethylstyrene, alkyl acrylate and acrylo nitrile.

In accordance with another feature of present invention the porous hydrophobic polymer includes a hyper-crosslinked polystyrene prepared by post-crosslinking of a macroporous styrene-divinylbenzene copolymer swollen in a solvent.

Some materials of this type are disclosed in patent application Ser. Nos. 09/019,583 and 09/019,584.

In accordance with still another feature of the invention the withdrawn dialysis solution with toxins is passed along an ultrafiltration membrane with vacuum applied at opposite side, to remove excess water and partially small toxic molecules.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view showing a diagram of the inventive method for peritoneal dialysis in accordance with the present invention.

DESCRIPTION OF PREFERRED EMBODIMENTS

In accordance with the present invention, peritoneal dialysis is performed by introducing a dialysis solution into the peritoneal cavity through an indwelling catheter. Then the dialysis solution is allowed to dwell in the peritoneal cavity for a period of time to provide diffusion through an inner lining of an abdominal cavity with exchange of components between a microcirculation of a peritoneum and a dialysis solution. The dialysis solution is then withdrawn from the peritoneal cavity with toxins and, in the new inventive way, passed through a material which has a size, a shape, and a structure selected so as to remove the toxicants in a molecular range of 300–30,000 Dalton from the dialysis fluid. The thusly purified peritoneal spent fluid is then returned to the patient.

The above-specified material effectively removes the pool of middle-sized molecules, as can be determined by spectrophotometric measurements. In the drawings Reference Numeral 1 identifies a patient, while Reference Numeral 2 identifies a device which contains the material and is formed for example as a cartridge.

In accordance with another feature of the present invention, the method further includes passing the withdrawn dialysis fluid with toxicants along a dialysis membrane for removing excess water and small toxic molecules, before returning the withdrawn dialysis fluid to the patient. Reference numeral 3 identifies such a device that contains the polymeric dialysis membrane, which is permeable to excess water and small toxic molecules, but not to larger protein molecules. The clearance here is achieved by diffusion and filtration (convection) mechanisms characteristic of conventional dialysis procedure. The latter requires a special dialysis solutions to be passed along the opposite side of the semipermiable membrane.

In some cases, when the concentration of the smaller toxic compounds in the dialysate liquid is considered to be well below the acceptable level, the removal of excess water (together with a portion of dissolved small toxic molecules) can be achieved in a more simple manner, namely, by applying vacuum on the opposite side of the semipermiable dialysis membrane 3'. In this simplified mode, the whole purification device would provide removal of excess water and middle size toxins as well as a partial removal of small toxic molecules.

The adsorbing material 2 represents a neutral polystyrenic or polyacrylic material with a highly developed inner surface area of above 400 square meter per gram and a broad pore size distribution that extends from macropores through an enhanced portion of mesopores to micropores. The macropores of over 20 nm in diameter provide high mass transfer properties to the material, the mesopores in the range between 2 and 20 nm are responsible for efficient adsorption of toxic proteins and other middle-size toxins that appear in the spent peritoneal dialysate, whereas the micropores below 2 nm in diameter adsorb smaller toxin molecules and, in a possible combination with dialysis, sufficiently contribute to the purification of the peritoneal dialysate fluid.

Macroporous styrene-divinylbenzene copolymers represent the most popular type of neutral polymeric adsorbing materials. Many companies manufacture adsorbents of this category, Amberlite XAD-4 (by Rohm and Haas) being probably the best known one. Equally interesting, though less frequently used, are macroporous adsorbing materials manufactured by copolymerization of divinylbenzene (DVB) with other monomers, e.g., buthyl methacrylate, acrylo nitrile and others. In order to provide porous structure to the material formed as the result of copolymerization of the monomer mixture, the latter must contain sufficient amounts of a porogen, i.e., an organic solvent that is miscible with the monomers, but does not participate in the polymerization and thus remains included in the network of the final polymer. After removal of the porogen, the remaining free space represents the pores of the sorbent obtained.

In accordance with the present invention, the broad pore size distribution and enhanced portion of mesopores in the material are obtained by using mixed solvents as the porogen. The mixture should contain a component with a high solvating power toward the polymer formed and a component that precipitates the polymer and causes micro-phase separation. It is important that the total composition of the porogen mixture is tuned in such a manner that the phase separation of the reaction mixture takes place after the major part of the initial co-monomers (over 50%) are consumed. Another important condition of obtaining material with a suitable pore size distribution is the relatively high content of conformationally rigid crosslinking agent in the initial comonomer mixture, above 20 weight percent of divinyl-benzene or diisopropenylbenzene. At lower crosslinking densities, the porous architecture of the network would be unstable, so that meso and especially micropores in the network would collapse during thermal treatment of the material, for instance, during thermal sterilization.

Another type of porous neutral polymeric material suitable for purification of peritoneal dialysate fluids is hypercrosslinked polystyrene. It is produced by an extensive post-crosslinking of macroporous styrene-divinylbenzene copolymers in the presence of a good solvating media. Usually the initial macroporous copolymer contains less than 25% DVB, preferably 5 to 15% DVB. It is then subjected to chloromethylation and finally heated in the presence of a Friedel-Crafts catalyst in a good solvating media. The initial copolymer, in strongly swollen state, can alternatively be directly post-crosslinked with a suitable bifunctional crosslinking reagent.

Some materials of the both above types were disclosed in an earlier patent application, Ser. No. 08/756,445. There, however, the outer surface of the adsorbent beads needed to be chemically modified, in order to enhance the hemocompatibility of the beads. Fortunately, this additional surface modification is not required for the purification of the spent peritoneal dialysate solution.

The material in accordance with the present invention is a porous hydrophobic polymer with a broad pore size distribution and an enhanced portion of meso-and micropores.

In the following examples, a mostly mesoporous divinylbenzene-ethylstyrene-styrene copolymer, a styrene-diisopropenylbenzene copolymer, a copolymer of DVB with buthyl methacrylate, and hypercrosslinked polystyrene materials were prepared. They effectively remove the pool of middle-sized molecules, as could be easily followed by conventional spectrophotometric measurements.

EXAMPLE 1

Into a seven-liter four-necked round-bottom flask equipped with a stirrer, a thermometer and a reflux condenser, is placed the solution of 8.4 g polyvinyl alcohol-type technical grade emulsion stabilizer GM-14 in four liters of deionized water (aqueous phase). The solution of 260 ml divinylbenzene, 140 ml ethylvinylbenzene, 250 ml toluene, 250 ml n-octane and 2.94 g benzoyl peroxide (organic phase) is then added to the aqueous phase on stirring at room temperature. In 20 min, the temperature is raised to 80° C. The reaction is carried out at 80 ° C. for 8 hours and at 90–92° C. for an additional 2 hours. After accomplishing the copolymerization, the stabilizer is rigorously washed out with hot water (60 to 80° C.) and the above organic solvents are removed by steam distillation. The beads obtained are filtered, washed with 1 l dioxane and with deionized water.

The polymer obtained in Example 1 displayed an apparent inner surface area of 1200 sq.m/g and total pore volume of 0.8 ml/g, increased its volume in ethanol by a factor of 1.3, adsorbed Cytochrome C from a phosphate buffer solution in an amount of 32–34 mg per 1 g of the polymer, efficiently removed beta2-microglobuline from blood of patients on chronic dialysis treatment (the blood was not returned to the patient). Individual spherical beads of the polymer of 0.4–0.63 mm in diameter were mechanically destroyed at a loading of 450 plus/minus 50 g.

EXAMPLE 2

As in Example 1, taking 220 ml divinylbenzene, 180 ml ethylvinylbenzene, 150 ml toluene, 150 ml n-octane and 3.0 g benzoyl peroxide as the organic phase. Inner surface area of the product obtained amounts to 1000 sq.m/g, volume swelling with ethanol amounts to 1.25.

EXAMPLE 3

As in Example 1, taking organic phase consisting of 320 ml divinylbenzene, 80 ml ethylvynylbenzene, 600 ml toluene, 400 ml iso-octane and 3 g bis-azoisobutyric nitrile. Inner surface area of the product obtained amounts to 1050 sq.m/g, volume swelling with ethanol amounts to 1.5.

EXAMPLE 4

As in Example 1, taking 250 ml benzene and 250 ml methanol, instead of toluene and n-octane, as the porogen for the preparation of organic phase. Inner surface area of the product obtained amounts to 800 sq.m/g. Volume swelling with ethanol amounts to 1.3

EXAMPLE 5

As in Example 1, taking 200 ml ethylene dichloride and 120 ml n-hexane as the porogen. Inner surface area of the product obtained amounts to 1000 sq.m/g. Volume swelling with ethanol amounts to 1.3.

EXAMPLE 6

As in Example 1, taking the mixture of 400 ml cyclohexane and 100 ml methanol as the porogen. Inner surface area of the product obtained amounts to 800 sq.m/g. Volume swelling with ethanol amounts to 1.2.

EXAMPLE 7

A solution of 130 g styrene, 130 g diisopropenylbenzene (a mixture of para and metha-isomers of about 1:1) and 2.5 g benzoyl peroxide in a mixture of 300 ml toluene and 100 ml iso-amyl alcohol was suspended in 4 liters of pure water containing 1% cellulose stabilizer. After 30 min stirring at room temperature, the mixture was heated at 40° C. for 1 hour, 60° C. for 2 hours, 80° C. for 5 hours and 96° C. for 2 hours. After cooling the mixture to room temperature, the beads of the material obtained were filtered and washed with hot water, methanol and water.

EXAMPLE 8

A solution of 75 g buthyl acrylate, 51 g divinylbenzene (a mixture of para and metha-isomers of about 1:1) and 1 g benzoyl peroxide in a mixture of 200 ml of toluene and 50 ml octane was suspended in 2.4 liters of pure water containing 15 g of cellulose stabilizer at room temperature. After 30 min stirring, the mixture was heated stepwise at 60, 80 and 95° C. within 3 hours for each temperature. After cooling to room temperature, the beads obtained were filtered, washed with hot water, methanol and water.

EXAMPLE 9

To a solution of 87.6 g xylylene dichloride (0.5 mol) in 600 ml dry ethylene dichloride 104 g (1 mol) of styrene copolymer with 0.5% divinylbenzene were added, the suspension was agitated for 1 hr and supplied with a solution of 116.8 ml tin tetrachloride (1 mol) in 100 ml ethylene dichloride. The reaction mixture was then heated for 10 hr at 80° C., the polymer was filtered and carefully washed with acetone, a mixture of acetone with 0.5 N HCl, 0.5 N HCl and water until no chloride ions were detected in the filtrate. The product dried in vacuum represented micro- and mesoporous hypercrosslinked polystyrene. It contained 0.65% pendant unreacted chlorine and displayed an inner surface area as high as 980 m$^2$/g.

EXAMPLE 10

To a suspension of 104 g (1 mol) of a macroporous styrene copolymer with 4% divinylbenzene in 500 ml dry ethylene dichloride a solution of 76 ml (1 mol) monochlorodimethyl ether and 116.8 ml (1 mol) tin tetrachloride in 100 ml ethylene dichloride was added. The mixture was then heated at 80° C. for 10 hr., the polymer was filtered and carefully washed with acetone, a mixture of acetone with 0.5 N HCl, 0.5 N HCl and water until no chloride ions were detected in the filtrate. The product dried in vacuum represented biporous hypercrosslinked polystyrene and contained 3.88% pendant unreacted chloride. The above extensive post-crosslinking resulted in the increase of its inner surface area from 120 to 1,265 m2/g.

It will be understood that each of the elements described above, or two or more together, may also find a useful application in other types of methods differing from the types described above.

While the invention has been illustrated and described as embodied in a method of peritoneal dialysis, it is not intended to be limited to the details shown, since various modifications and structural changes may be made without departing in any way from the spirit of the present invention.

Without further analysis, the foregoing will fully reveal the substance of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

What is claimed is:

1. A method of peritoneal dialysis, comprising the steps of introducing a dialysis solution into a peritoneal cavity; allowing the dialysis solution to dwell in the peritoneal cavity for a period of time to provide diffusion through an inner lining of an abdominal cavity with exchange of components between a microcirculation of a peritoneum and the dialysis solution; then withdrawing the dialysis solution from the peritoneal cavity with toxins; passing the dialysis solution with toxins through an adsorbent porous hydrophobic polymeric material composed of beads with pores which has a size, shape, and structure selected so as to remove the toxicants in a molecular range of 300–30,000 Dalton from the dialysis solution; and returning the thusly purified peritoneal dialysis solution to the patient.

2. A method as defined in claim 1, wherein said adsorbent porous hydrophobic polymeric material has an enhanced proportion of pores in a diameter range between 1 and 10 nm.

3. A method as defined in claim 2, wherein said porous hydrophobic polymeric material includes a copolymer of a crosslinking divinyl compound selected from the group consisting of divinylbenzene and diisopropenylbenzene and a monovinyl compound selected from the group consisting of styrene, ethylstyrene, alkyl acrylate and acrylo nitrile.

4. A method as defined in claim 2, wherein said porous hydrophobic polymeric material includes a hypercrosslinked polystyrene prepared by post-crosslinking of a macroporous styrene-divinylbenzene copolymer swollen in a solvent.

* * * * *